United States Patent [19]

Yu

[11] 4,358,603
[45] Nov. 9, 1982

[54] ACETAL STABILIZED PROSTAGLANDIN COMPOSITIONS

[75] Inventor: Cheng-Der Yu, Mountain View, Calif.

[73] Assignee: Syntex (U.S.A.) Inc., Palo Alto, Calif.

[21] Appl. No.: 254,824

[22] Filed: Apr. 16, 1981

[51] Int. Cl.$^3$ .................. C07C 177/00; A61K 31/557
[52] U.S. Cl. .......................................... 560/2; 562/503
[58] Field of Search ................... 560/2, 121; 562/503; 424/305, 317

[56] References Cited

U.S. PATENT DOCUMENTS 3,833,612  9/1974  Wendler et al. .................... 562/503
4,178,454  12/1979  Naruto et al. ........................... 560/2

Primary Examiner—Robert Gerstl
Attorney, Agent, or Firm—James M. Kanagy; Alan M. Krubiner; Tom M. Moran

[57] ABSTRACT

Degradation of prostaglandins in anhydrous or aqueous pharmaceutically acceptable, water-miscible alcohol solutions is prevented by adding a stabilizing amount of a pharmaceutically acceptable acetal.

27 Claims, No Drawings

ACETAL STABILIZED PROSTAGLANDIN COMPOSITIONS

BACKGROUND OF THE INVENTION

1. Field of the Invention

This invention relates to stable prostaglandin solutions and to a method for stabilizing prostaglandins in solution. More specifically, it relates to acetal stabilized anhydrous or aqueous alcoholic prostaglandin solutions.

2. Related Disclosures

Prostaglandins have classically been described as chemically related 20 carbon chain hydroxy fatty acids having the basic skeleton of prostanoic acid:

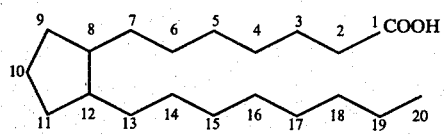

this structure is the basis for prostaglandin numbering and nomenclature.

Naturally occuring prostaglandins are derivatives of prostanoic acid. For descriptive purposes, four types are recognized. The type distinction is based primarily on pentane ring subtituents and structural orientation. Although they can be named as derivatives of prostanoic acid, they are conventionally referred to by the letters A, B, E and F. Prostaglandins having an hydroxyl group at the C-11 position and a keto group at the C-9 position are known as PGE or PGE-type compounds. Those having hydroxyl groups at C-9 and C-11 are known as the PGF series and are further designated by an $\alpha$ or $\beta$ suffix to indicate the configuration of the hydroxyl group at said position. Series A and B have a keto group at C-9 and a double bond between C-10 and C-11 or C-8 and C-12 respectively. The natural compounds are the $\alpha$-hydroxy substituted compounds. Prostaglandins may contain different series of unsaturation in the molecule, particularly at C-5, C-13 and C-17. The unsaturation is also indicated by a suffix. Thus, for example, $PGF_1$ and $PGE_1$ series refer to prostanoic acids having a trans-olefin bond at the C-13 position, while the $PGF_2$ and $PGE_2$ series refer to prostadienoic acids having a cis-olefin bond at the C-5 position and a trans-olefin bond at the C-13 position. For a review on prostaglandins and the definition of primary prostaglandins, see for example, S. Bergstrom, Recent Progress in Hormone Research 22, pp. 153–175 (1966) and Science 157, p. 382 (1967) by the same author.

Prostaglandins generally act to stimulate gastrointestional and reproductive smooth muscles, affect relaxation and contraction of respiratory smooth muscle, are hypotensives, and inhibit lipolysis of fatty acids, gastric acid secretion and blood platelet aggregation. There is not a precise structure-activity relationship in the prostaglandin family as much cross-activity is evident.

A great number of studies have been undertaken to enhance, extend and otherwise modify the activity of naturally occurring prostanoic acids. The majority of these studies have focused on modification of two areas, the two side chains and substituents attached to the cyclopropane moiety [see, for example, U. Axen et al, Synthesis Vol. 1, John Wiley and Sons Inc., New York, N.Y. 1973 and P. H. Bently, Chem. Soc. Reviews, 2, 29 (1973)].

Of special interest to this invention is that group of prostaglandins which are labile in most standard pharmaceutical compositions, particularly PGE compounds and PGE-type compounds. In many instances the cyclopentane ring substituents substantially affect the prostaglandin's level of activity. Compounds which loose an oxygen from either C-9 or C-11 on the cyclopentane ring or which have these positions altered show altered levels of activity. For instance $PGE_{2\alpha}$, which has a carbonyl group at C-9 and an hydroxyl group at C-11 stimulates smooth muscle tissue but loss of the C-11 hydroxyl group to give a double bond in the cyclopentane ring, the PGA or PGB forms, show little or no such activity. This conversion is chemically facile because of the presence of the carbonyl group at C-9 in the PGE and PGE-type compounds which makes the hydroxyl group at C-11 labile to either base or acid dehydroxylation. The product of this dehydroxylation is a double bond conjugated with the carbonyl group of C-9, a stable chemical entity. Under acid conditions PGE-type compounds convert readily to the PGA form. Basic conditions cause PGE-type compounds to dehydroxylate and rearrange to the PGB form. In the case of $PGE_2$ type compounds this latter form is particularly stable because the C-9 carbonyl is now conjugated with the C-8/C-12 and C-13/C-14 double bonds. Similiar degradation patterns have been observed in most compounds which have PGE-type cyclopentane ring substituents.

Initial efforts at providing easily dispensible dose formulations of prostaglandins, particularly for PGE-type compounds, met with difficulty. Aqueous PGE solutions were found to undergo rapid loss of activity when stored at temperatures above 0° C. at any pH, but particularly under alkaline conditions. Hydrous solutions adjusted to pH 5–7 were found to be most stable but loss of activity was still so rapid, drug concentrations after several months were very uncertain. Even in neutral or neat solutions there was found gradual degradation. Similiar rapid degradation under these conditions have been observed in most compounds which have PGE-type cyclopentane ring substituents.

Various attempts have been made to formulate stable solutions of PGE-type compounds. Stabilization of these compounds has been observed in some solutions and in solid form at −20° C. or lower. More practical and usable alternative methods for stabilizing these prostaglandins have been developed and are described, for example, in U.S. Pat. Nos. 3,749,800; 3,826,823; 3,829,579; 3,851,052; 3,833,725; and 4,221,793. These patents teach the use of such solvents as lower molecular weight alcohols, polyalkylene glycols, dialkylated polyalkylene glycols, triacetin, dimethylacetamide and triethylcitrate. All these disclosure contain the limitation that the solvent and the resulting drug solution must be anhydrous, i.e. contain less than 0.5% water, in order to achieve stable formulations. The dialkylated polyalkylene glycols are excepted from this particular limitation, but prefered formulations using these solvents contain less than 0.5% water.

It has now been found that prostaglandins in general and specifically PGE and PGE-type prostaglandin compounds can be prepared as stable compositions in aqueous alcoholic solutions by including in the preparation a minor amount of a pharmaceutically acceptable acetal. Such compositions are particularly adaptable for injectable unit dose preparations requiring no further dilution because of the high amount of water, upwards of 50% (w/v), which may be included in these acetal stabilized compositions.

SUMMARY

In the broadest aspect, this invention consists of a stable prostaglandin composition characterized by the presence of an acetal. One aspect of this invention is concerned with novel stable prostaglandin compositions comprising a prostaglandin dissolved in an anhydrous or aqueous pharmaceutically acceptable, water-miscible alcohol solvents containing a stabilizing amount of a pharmaceutically acceptable acetal. A further aspect is a method for stabilizing a prostaglandin solution which method comprises mixing a stabilizing amount of a pharmaceutically acceptable acetal with a prostaglandin and an anhydrous or hydrous pharmaceutically acceptable, water miscible alcohol.

DETAILED DESCRIPTION OF THE INVENTION

The broadest embodiment of this invention involves dissolving any prostaglandin compound, but particularly a PGE or PGE-type compound, in a solvent made up of a mono or polyhydric alcohol and an acetal or a mono or polyhydric alcohol, water and an acetal. The acetal may be present in an amount of about 0.5% to 25% weight/volume (w/v) regardless of the alcohol or alcohol/water solvent. Where an aqueous alcohol solvent is used, water may be present in an amount of up to 50% (w/v) of the acetal/alcohol/water mixture. Any amount of prostaglandin between about 0.001 and 100 mg/ml may be formulated in this solvent, dependent only on the solubility of a particular prostaglandin in a particular solvent composition. Acceptable alcohols are any pharmaceutically acceptable water-miscible solvents having one or more hydroxyl groups. Any pharmaceutically acceptable acetal soluble in the described anhydrous or aqueous alcohol solvents can be used as a stabilizing agent in the practice of this invention.

Preparation of stable prostaglandin compositions, especially multiple dose injectable prostaglandin solutions, has been a desired goal in the pharmaceutical industry since the advent of prostaglandin research. Most prostaglandins are sparingly soluble in water but are soluble in certain organic solvent/water mixtures, particularly alcohols and closely related solvents. While it would be most desireable to use organic solvent/water mixtures as solvents for direct injection of drugs such as prostaglandins to reduce patient or test subject exposure to the potentially toxic effect of the organic solvent, many prostaglandins, particularly the PGE-type, are very labile in water-containing solutions. Solutions containing more than 1 or 2% water have invariably shown significant prostaglandin E-type degradation within several days. Even the trace amounts of water normally present in so-called anhydrous organic solvents has long been the bane of formulation chemists faced with the task of preparing prostaglandin E-type solutions having long-term stability. It has now been discovered that stable organic solvent based prostaglandin solutions may be prepared, even though more than 0.5% to 5% water is present, by adding a pharmaceutically acceptable acetal to the solution. Acetals' stabilizing effect is even seen and is most pronounced when they are added to anhydrous organic solvents.

Generically, acetals are that group of diether compounds resulting from the reaction between an aldehyde and two alcohol moieties to give a compound having the general formula $R_1CH(OR_2)_2$. For the purpose of this invention the word "acetal" should be understood to mean those compounds according to this formula wherein $R_1$ is an alkyl radical of 1 to 4 carbon atoms or phenyl and $R_2$ is an alkyl radical of 1 to 4 carbon atoms. Herein an alkyl radical of 1 to 4 carbon atoms is, for example, methyl, ethyl, propyl, butyl, or the like.

The preferred acetals of this invention are those wherein $R_1$ is methyl or phenyl and $R_2$ is ethyl.

The compound where $R_1$ is methyl and $R_2$ is ethyl is most preferred. It is variously known as acetaldehyde diethyl acetal, acetaldehyde diethyl acetal or simply, acetal. Acetaldehyde diethyl acetal is a volatile liquid with a boiling point of 102.7° C. at STP. It is miscible with ethanol and alcohol/water solutions to 40% water. Solubility in water is 5 g per 100 ml. Classically it is prepared from acetalhyde and ethanol in the presence of anhydrous calcium chloride or of small quantities of mineral acid. See *Organic Synthesis* 3, 1 (1923).

The only limitation being placed on the selection of an acetal from the described groups is that it have no deleterious or untoward effect on the subject at the concentrations and in the final dosage form in which it would be administered to a subject during the course of a usual treatment regime. This limitation is to be based on the solution as finally prepared for administration and the route by which it is to be administered.

Acetals are not intended to be the major component of the stable prostaglandin solutions disclosed and discussed herein. Their usefulness here is analogous to that of a preservative or antioxidant. That is, a minor amount of a pharmaceutically acceptable acetal is added to an anhydrous or aqueous alcohol solvent system specifically for the purpose of stabilizing prostaglandins dissolved therein. Whatever solubilizing effects, or other effects, this small amount of acetal may have on prostaglandins in the various alcohol or alcohol/water solvent mixtures is incidental to the stabilizing effect they exhibit on prostaglandins in these solvents.

A small amount, or a stabilizing amount, of an acetal is any amount between about 0.1% and 25% (w/v) of the finally prepared prostaglandin solution. Preferably the acetal concentration will fall between about 0.5% and 10%. The most preferred amounts are those acetal concentrations wherein the acetal is present in the finally prepared prostaglandin solution in an amount between about 2% and 7% (w/v).

Research to find pharmaceutically acceptable organic solvents which can be for use in preparing stable prostaglandin compositions has been proceeding apace since the dawn of prostaglandin chemistry and pharmacology. Because of the intense interest in this area a great number of solvents and solvent combinations have been proposed and patented. The most successful are organic solvents containing an oxygen functionality such as alcohols, ethers, polyethers, esters, or organic solvents which contain two of these functions. Certain other organic solvents, for example dipolar aprotic solvents (U.S. Pat. No. 3,829,579), have been disclosed as appropriate solvents for preparing stable PGE and PGE-type compounds. Generally these solvents, except for the dipolar aprotic solvents, are simple alcohols, polyhydric alcohols such as glycols or polyalkylene glycols (U.S. Pat. No. 3,749,800), dialkylated polyalkylene glycols (U.S. Pat. No. 3,833,725), the tri-acetic acid ester of glycerol (U.S. Pat. No. 3,996,962) and triethyl citrate (U.S. Pat. No. 4,211,793).

While the concept of adding acetals to prostaglandin solutions to enhance active ingredient stability is applicable to all these solvents in both their anhydrous and hydrous forms, particularly where the active ingredient is a PGE or PGE-type compound, the invention has its greatest utility when applied to ethers, esters, aldehydes, ketones, alcohols, dialkyl carbonates, carboxylic acids and other similiar oxygen function containing organic solvents. This is especially true where the organic solvent is a pharmaceutically acceptable, water-miscible alcohol.

The pharmaceutical acceptability of an alcohol is to be based on the solution as administered rather than on the stock solution. Some anhydrous solutions, for example, might not be pharmacologically acceptable in the undiluted stock solution form but is very much so when diluted with a large volume of water as in enteral or parenteral administration. Thus a pharmaceutically acceptable alcohol as used herein is one which on dilution into another aqueous vehicle or another pharmaceutically acceptable solvent causes no untoward pharmacodynamic effect.

The phrase water-miscible is intended to cover those alcohols which mix with water in all proportions or which are so highly soluble in water that they behave as if they were completely miscible with water. Such alcohols may be any solvent which contains one or more hydroxyl groups regardless of whether or not the solvent is named as an alcohol. This group of solvents includes not only the simple alcohols such as ethanol, isopropanol, hexanol and octanol but extends to such polyhydric alcohols as 1,3-butanediol, propylene glycol, glycerol, polyethylene glycol having a molecular weight between about 200 and 600, and the like. Triethyl citrate is also to be included within this definition.

The stabilizing effect of an acetal on a prostaglandin-alcohol solution is observed in anhydrous solutions as well as in water-containing solutions. For instance while anhydrous ethanolic prostaglandin solutions, that is ethanol solutions which contain less than 0.1% water, exhibit generally acceptable stability profiles prostaglandin decomposition can be further retarded and delayed by adding an acetal to the solution. A similar phenomena is seen with most other prostaglandin stabilizing solvents but, as noted above, is most pronounced for alcohols and hydroxyl-containing solvents.

When a stabilizing amount of an acetal is added to the mixture, water in an amount up to 50% (w/v) may be mixed with these organic solvents and prostaglandins can be dissolved therein without incurring unacceptable degradation during extended storage. While acetals will adequately stabilize prostaglandins in alcohol solutions containing up to 50% water it is frequently preferable to keep the amount of water to 25% or less but most preferably 10% or less.

In the practice of this invention prostaglandin concentrations may range anywhere from 0.001 to 100 mg/ml of solvent. Within this range preferred active ingredient concentrations will vary with the relative activity of the drug, its solubility in a given solvent profile, and the amount of drug to be administered per unit dose. Such considerations are best determined by the formulator in conjunction with the known solubility, activity data and treatment regime to be achieved at the time of formulation. It is preferred that the concentration of the PGE or PGE-type compound in whatever solvent is employed be in the range of 0.01 to 25 mg per ml, although for those PGE-type compounds which are highly active, lower concentration can be used. An especially preferred concentration range is 0.01 to 5 mg per ml.

The acetal containing solvents of this invention may be used to stabilize all types of prostaglandin compounds but have the greatest utility for PGE compounds and PGE-type compounds. The phrase "PGE compounds" refers to those naturally occuring compounds which are derivatives of prostanoic acid and which have a C-9 carbonyl substituent and C-11 and C-15 hydroxyl substituents. These compounds have varying degrees of unsaturation as discussed above and all are intended to be included within the scope of the phrase "PGE compounds". There is intended to be included in this definition $PGE_1$, $PGE_2$, $PGE_3$ and dihydro-$PGE_1$ compounds. Esters of these compounds have been synthetically prepared, see for example U.S. Pat. Nos. 3,069,332 and 3,598,858.

There also have been prepared many compounds which retain the C-9 carbonyl and C-11 hydroxyl cyclopentane ring structural features but wherein the side chains have been modified; and which cause at least part of the biological response caused by PGE compounds. These compounds are intended to be included within the scope of this invention and are covered herein by the phrase "PGE-type compounds". Modified compounds differ from PGE compounds in one or more structural aspects, for example, in having one or more substituents, for example, alkyl, fluoro, phenyl, or cycloalkyl, on one or both side chains; in having fewer or more methylene groups in one or both side chains; in having a hetero atom, for example, oxygen in place of a side-chain methylene group; in having cis rather than a trans or a trans rather than a cis configuration for a side-chain carbon-carbon double bond; in having allenic double bonds in one side chain; or in any combination of those structural aspects. As examples of art which discloses such PGE-type compounds and others, see U.S. Pat. Nos. 3,639,463; 3,759,978; 3,767,695; 3,781,325; 3,804,889; 3,812,179; 3,813,433; 3,833,640; 3,835,180; 3,842,118; 3,847,966; 3,849,487; 3,855,270; 3,864,387; and 4,178,457. See also German Offenlegungschrift Nos. 1,937,675; 1,937,921; 2,011,969; 2,036,471; 2,118,686; 2,121,980; 2,144,048; 2,150,361; 2,154,309; 2,165,184; 2,209,990; 2,217,044; 2,221,443; 2,317,019; 2,320,552; 2,322,673; 2,332,400; 2,345,685; 2,423,155 and 2,423,156. See also French Pat. No. 2,119,855, Belgian Pat. Nos. 779,898 and 782,822.

Also, for the purposes of this invention, it is intended to include racemic mixtures as well as resolved enantiomers of both PGE and PGE-type compounds.

In both instances it should be understood that not only the carboxylic acids are to be included but also esters of said compounds. Those esters wherein the esterifying radical is alkyl of one to 12 carbon atoms, inclusive, cycloalkyl of 3 to 10 carbon atoms, aralkyl of 7 to 12 carbon atoms, phenyl, and phenyl substituted with 1, 2 or 3 chloro or alkyl of 1 to 4 carbon atoms are typical. Alkyl esters of 1 to 4 carbon atoms are particularly useful, especially methyl and ethyl esters.

Pharmaceutically acceptable salts of both compound groups are also to be included. These salts may be prepared from pharmaceutically acceptable non-toxic bases, including inorganic and organic bases. Salts derived from inorganic bases include, preferably, ammonium, potassium, sodium, calcium and magnesium salts. Preferred organic bases are isopropylamine, diethylamine, ethanolamine, peperidine, tromethamine, choline and caffine.

Solutions stabilized by the presence of acetals can be administered to animal or human subjects by any of the routes known to be useful for administration of prostaglandin type compounds. Solutions of this invention which contain 20% to 50% water may, in certain instances, be administered by direct injection into the blood stream, for example, by intravenous or intraerterial injection or by infusion.

Alternatively, acetal stabilized solutions are injected subcutaneously or intramuscularly. Such solutions can be incorporated into a pack capable of generating an aerosal containing small droplets of the acetal stabilized solution for the treatment of the upper respiratory tract, for example, in the treatment of asthma. Solutions stabilized with an acetal can be administered by styrine or other known appropriate mechanical means into the rectum, the vagina, the ear canal, or the nostril to cause desired medical results which are known to occur when prostaglandin compounds are administered to these areas. Additionally, acetals may be incorporated into known suppository bases for rectal and vaginal administration of prostaglandin compounds. Acetals are equally appropriate for stabilizing orally administrable prostaglandin solutions and capsules including enteric coated capsules and water-dispersible materials such as, for example, gelatin.

SPECIFIC EMBODIMENTS

In the general case, the compositions of this invention are prepared by first preparing the acetal containing solvent and then mixing in by some mechanical means an amount of prostaglandin which will provide the desired final concentration. While this is the suggested sequence for preparing the stable solutions of this invention, it should be understood that this is not the only sequence available. For example, the acetal and alcohol could be combined first and water added to achieve the desired solvent profile. Alternatively water and alcohol can be combined first, followed by the addition of an acetal to realize solutions with respective solvent or acetal concentrations which fall within stated ranges. While the mentioned processes imply that the drug is always added last, such need not be the case. The active ingredient can be predissolved in any of the single or combined solvents and then brought to volume with the remaining solvent or solvents. No possible solvent preparation sequence or solvent/drug preparation sequences are excluded herein.

EXAMPLE I

Acetaldehyde diethyl acetal, 5 grams, is added to a 100 ml volumetric flask and brought to volume with anhydrous propylene glycol. Mechanical stirring is used to form a homogenous solution. To 10 ml of this solvent at ambient temperature is added 5 mg of (dl)-11α,15α-dihydroxy-16-phenoxy-17,18,19,20-tetranor-9-oxoprosta-4,5,13(t)-trienoic acid methyl ester. The mixture is stirred by a blade-type stirrer for 2 hours to give a homogenous mixture.

EXAMPLE II

An anhydrous ethanol-acetal solvent mixture is prepared by mixing 5 g of acetaldehyde diethyl acetal with a quantity of ethanol, USP, sufficient to make 100 ml. The 16-phenoxy-trienoic acid methyl ester described in Example I, 900 ug, was added to a 10 ml aliquot of this solvent at ambient temperature. A homogenous mixture was obtained by stirring the mixture for about 2 hours with a blade type stirrer.

EXAMPLE III

The formulation of a 0.5 mg/ml 16-phenoxy-trienoic acid methyl ester described in Example I in a 5% aqueous ethanol solution containing 5% acetal is prepared by weighing 5 g of water and 5 g of acetaldehyde diethyl acetal into a 100 ml volumetric flask and then a quantity of ethanol, USP, sufficient to make 100 ml is added. Mechanical stirring is used to form a homogeneous solution. Five mg of the trienoic acid methyl ester described in Example I is stirred into a 10 ml aliquot of the acetal containing hydrous ethanol solution.

EXAMPLE IV

As an example of the stablizing effect acetals exhibit when added to anhydrous and aqueous organic solvent solutions of PGE-type compounds, a solution of (dl)-11α,15α-dihydroxy-16-phenoxy-17,18,19,20-tetranor-9-oxoprosta-4,5,13(t)-trienoic acid methyl ester at a concentration of 0.5 mg/ml was dissolved in propylene glycol containing varying amounts of water and 5% (w/v) acetaldehyde diethyl acetal. All compositions were stored at 45° C., aliquots being analyzed at various time points through 30 days. The data in Table I (test) and Table II (control) was obtained from this study.

TABLE I

Stability of an E-type* prostaglandin (0.5mg/ml) in propylene glycol/water/(5%) acetaldehyde diethyl acetal stored at 45° C.

| | % Drug Remaining | | | | | | |
|---|---|---|---|---|---|---|---|
| | H$_2$O Content | | | | | | |
| Days | 0% | 5% | 10% | 20% | 30% | 40% | 50% |
| 0 | 100 | 100 | 100 | 100 | 100 | 100 | 100 |
| 3 | 105.8 | 107.2 | 108.8 | 108.0 | 101.1 | 101.3 | 103.0 |
| 6 | 99.8 | 100.2 | 100.5 | 97.9 | 93.0 | 91.8 | 89.3 |
| 12 | 98.1 | 96.8 | 98.6 | 93.8 | 87.3 | 83.1 | 81.3 |
| 18 | 96.1 | 95.0 | 94.9 | 89.6 | 83.1 | 77.6 | 74.0 |
| 30 | 98.4 | 95.6 | 94.0 | 86.0 | — | — | — |

*(dl)-11α,15α-dihydroxy-16-phenoxy-17,18,19,20-tetranor-9-oxoprosta-4,5,13(t)-trienoic acid methyl ester.

TABLE II

Stability of an E-type* prostaglandin (0.5mg/ml) in propylene glycol/water stored at 45° C.

| | % Drug Remaining | | | | | | |
|---|---|---|---|---|---|---|---|
| | H$_2$O Content | | | | | | |
| Days | 0% | 5% | 10% | 20% | 30% | 40% | 50% |
| 0 | 100 | 100 | 100 | 100 | 100 | 100 | 100 |
| 3 | 95.0 | 90.7 | 90.4 | 91.3 | 85.3 | 73.2 | 69.6 |
| 6 | 99.0 | 84.7 | 84.7 | 79.0 | 77.0 | 71.0 | 52.9 |
| 11 | 81.1 | 73.7 | 75.9 | 64.8 | 50.4 | 39.4 | 34.9 |
| 14 | 80.4 | 68.0 | 72.4 | 58.4 | 50.9 | 38.8 | 28.3 |
| 30 | 62.6 | 45.4 | 47.2 | — | — | — | — |

*(dl)-11α,15α-dihydroxy-16-phenoxy-17,18,19,20-tetranor-9-oxoprosta-4,5,13(t)-trienoic acid methyl ester.

At this elevated temperature a very prounounced stabilizing effect can be seen in the anhydrous and low water content solutions at day 12 and thereafter. Acetaldehyde diethyl acetal effectively prevents significant degradation under these conditions where 10% water is present in the composition. At higher water concentrations the stabilizing effect is particularly noticeable in relation to the controls.

EXAMPLE V

Acetal's stabilizing effect can be equally well seen where ethanol is the organic solvent. Several solutions of the 16-phenoxy-trienoic acid methyl ester described in the above paragraph were formulated to contain 90 ug/ml of this prostaglandin in anhydrous ethanol, USP, and several ethanol/water mixtures with 5% acetaldehyde diethyl acetal added to each mixture. Table III contains the results observed after storage for 8 days at 60° C.

TABLE III

Stability of An E-type* Prostaglandin (0.09mg/ml) in ethanol/water/(5% w/v) acetaldehyde diethyl acetal stored 8 days at 60° C.

| ID | Water | Acetal | % Drug Remaining |
|----|-------|--------|------------------|
| A  | 0%    | 5%     | 98%              |
| B  | 0%    | 0%     | 46%              |
| C  | 1%    | 5%     | 98%              |
| D  | 0%    | 0%     | 41%              |

*(dl)-11α,15α-dihydroxy-16-phenoxy-17,18,19,20-tetranor-9-oxoprosto-4,5,13(t)-trienoic acid methyl ester.

These data show that at 60° C. there is little degradation in any of the acetaldehyde diethyl acetal containing compositions (A and C), while even the anhydrous ethanol control, (B), composition has undergone significant decomposition.

What is claimed is:

1. A stable prostaglandin composition comprising a prostaglandin dissolved in an anhydrous or aqueous pharmaceutically acceptable, water-miscible alcohol solution containing a stabilizing amount of a pharmaceutically acceptable acetal having the general formula $R_1CH(OR_2)_2$ wherein $R_1$ is an alkyl radical of 1 to 4 carbon atoms or phenyl and $R_2$ is an alkyl radical of 1 to 4 carbon atoms.

2. A composition according to claim 1 wherein said prostaglandin is present in an amount between 0.001 and 100 mg/ml; said solution comprises up to 50% (w/v) water; and said acetal is present in an amount between 0.1% to 25% (w/v).

3. A composition according to claim 2 wherein said prostaglandin is a PGE or PGE-type prostaglandin; said alcohol is ethanol, propylene glycol, glycerol, or polyethylene glycol molecular weight 200–600; and said acetal is acetaldehyde diethyl acetal or benzaldehyde diethyl acetal.

4. A composition according to claim 3 wherein said prostaglandin is present in an amount between 0.01 and 25 mg/ml; said solution comprises up to 25% water by weight; and said acetal is present in an amount between 0.5% to 10% (w/v).

5. A composition according to claim 4 wherein said alcohol is ethanol or propylene glycol; and said acetal is acetaldehyde diethyl acetal.

6. A composition according to claim 5 wherein said prostaglandin is present in an amount between 0.01 and 5 mg/ml; said solution comprises up to 10% water by weight; and said acetal is present in an amount of 2% to 7% (w/v).

7. A composition according to claim 6 wherein said prostaglandin is (dl)-11α,15α-dihydroxy-16-phenoxy-17,18,19,20-tetranor-9-oxoprosta-4,5,13(t)-trienoic acid methyl ester in an amount of 0.5 mg/ml; said alcohol solution comprises 5% (w/v) water in ethanol, and said acetaldehyde diethyl acetal is present in an amount of 5% (w/v).

8. A composition according to claim 2 wherein said solution contains less than 0.1% (w/v) water by weight.

9. A composition according to claim 8 wherein said prostaglandin is a PGE or PGE-type prostaglandin; said alcohol is ethanol, propylene glycol, glycerol, or polyethylene glycol molecular weight 200–600; and said acetal is acetaldehyde diethyl acetal or benzaldehyde diethyl acetal.

10. A composition according to claim 9 wherein said prostaglandin is present in an amount between 0.01 and 25 mg/ml; and said acetal is present in an amount between 0.5% to 10% (w/v).

11. A composition according to claim 10 wherein said alcohol is ethanol or propylene glycol; and said acetal is acetaldehyde diethyl acetal.

12. A composition according to claim 11 wherein said prostaglandin is present in an amount between 0.01 and 5 mg/ml; and said acetal is present in an amount of 2% to 7% (w/v).

13. A composition according to claim 1 wherein said composition is contained in a water-dispersible material suitable for oral administration.

14. A composition according to claim 1 wherein said composition is sterile and injectable, optionally admixed with an aqueous diluent.

15. A method for stabilizing a prostaglandin solution which method comprises mixing a stabilizing amount of a pharmaceutically acceptable acetal having the general formula $R_1CH(OR_2)_2$ wherein $R_1$ is an alkyl radical of 1 to 4 carbon atoms or phenyl and $R_2$ is an alkyl radical of 1 to 4 carbon atoms with a prostaglandin and an anhydrous or hydrous pharmaceutically acceptable, water-miscible alcohol.

16. A method according to claim 15 wherein said prostaglandin is present in an amount between 0.001 and 100 mg/ml; said solution comprises up to 50% (w/v) water; and said acetal is present in an amount between 0.1% to 25% (w/v).

17. The method of claim 16 wherein said prostaglandin is a PGE or PGE-type prostaglandin; said alcohol is ethanol, propylene glycol, glycerol, or poylethylene glycol molecular weight 200–600; and said acetal is acetaldehyde diethyl acetal or benzaldehyde diethyl acetal.

18. A method according to claim 17 wherein said prostaglandin is present in an amount between 0.01 and 25 mg/ml; said solution comprises up to 25% water by weight; and said acetal is present in an amount between 0.5% to 10% (w/v).

19. A method according to claim 18 wherein said alcohol is ethanol or propylene glycol; and said acetal is acetaldehyde diethyl acetal.

20. A method according to claim 19 wherein said prostaglandin is present in an amount between 0.01 and 5 mg/ml; said solution comprises up to 10% water by weight; and said acetal is present in an amount of 2% to 7% (w/v).

21. A method according to claim 20 wherein said prostaglandin is (dl)-11α,15α-dihydroxy-16-phenoxy-17,18,19,20-tetranor-9-oxoprosta-4,5,13(t)-trienoic acid methyl ester in an amount of 0.5 mg/ml; said alcohol solution comprises 5% (w/v) water in ethanol; and said acetal is present in an amount of 5% (w/v).

22. A method according to claim 15 wherein said solution contains less than 0.1% (w/v) water.

23. A method according to claim 22 wherein said prostaglandin is a PGE or PGE-type prostaglandin; said alcohol is ethanol, propylene glycol, glycerol, or polyethylene glycol molecular weight 200–600; and said acetal is acetaldehyde diethyl acetal or benzaldehyde diethyl acetal.

24. A method according to claim 23 wherein said prostaglandin is present in an amount between 0.01 and 25 mg/ml; and said acetal is present in an amount between 0.5% to 10% (w/v).

25. A method according to claim 24 wherein said alcohol is ethanol or propylene glycol; and said acetal is acetaldehyde diethyl acetal.

26. A method according to claim 25 wherein said prostaglandin is present in an amount between 0.01 and 5 mg/ml; and said acetal is present in an amount of 2% to 7% (w/v).

27. A method according to claim 25 wherein said prostaglandin is (dl)-11d, 15α-dihydroxy-16-phenoxy-17,18,19,20-tetranor-9-oxoprosta-4,5,13(t)-trienoic acid methyl ester in an amount of 0.5 mg/ml; and said acetal is present in an amount of 5% (w/v).

* * * * *